United States Patent [19]

Mori et al.

[11] Patent Number: 4,563,209
[45] Date of Patent: Jan. 7, 1986

[54] AQUATIC ORGANISM INHIBITING COMPOSITION

[75] Inventors: Kogoro Mori; Hideo Ohi, both of Shizuoka; Chihiro Yazawa, Kanagawa, all of Japan

[73] Assignee: Ihara Chemical Industry Co., Ltd., Tokyo, Japan

[21] Appl. No.: 313,249

[22] Filed: Oct. 21, 1981

Related U.S. Application Data

[62] Division of Ser. No. 165,122, Jun. 20, 1979, Pat. No. 4,318,730.

[30] Foreign Application Priority Data

Jan. 20, 1978 [JP] Japan ................................. 53-5029

[51] Int. Cl.⁴ ..................... A01N 55/04; A01N 43/36
[52] U.S. Cl. ............................ 71/66; 71/67; 71/95; 71/97
[58] Field of Search .............. 71/66, 67, 97, 65, 95, 71/82; 424/145, 274

[56] References Cited

U.S. PATENT DOCUMENTS

| | | | |
|---|---|---|---|
| 3,222,158 | 12/1965 | Sowa | 71/97 |
| 4,012,503 | 3/1977 | Freiman | 424/288 |
| 4,080,190 | 3/1978 | Law et al. | 71/97 |
| 4,122,271 | 10/1978 | Williams | 71/66 |
| 4,318,730 | 3/1982 | Mori et al. | 71/66 |

FOREIGN PATENT DOCUMENTS

197352  7/1967  U.S.S.R. ................................. 71/67

OTHER PUBLICATIONS

Mori et al. I, "Bismaleimide Antifouling Agents," 1977, CA 88, No. 165499z, (1978).
Mori et al. II, "N-Aryl-2-Substituted, etc.;" (1977), CA 88, No. 165,500t, (1978).
Mori et al. III, "Agent for Hindering the Adherence, etc," (1978), CA 106871s, (1978).

*Primary Examiner*—Glennon H. Hollrah
*Attorney, Agent, or Firm*—Oblon, Fisher, Spivak, McClelland & Maier

[57] ABSTRACT

The present invention relates to an aquatic organism inhibiting composition which comprises at least one N-arylmaleimide having the formula

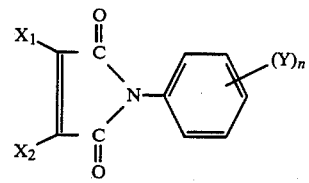

wherein $X_1$ and $X_2$ are the same or different and respectively represent hydrogen or a halogen atom; and Y represents a halogen atom or an alkyl or a lower alkoxy group and n is 0 or an integer of 1 to 3, and at least one organo-tin compound selected from the group consisting of bis(tri-n-butyl tin)mesodibromosuccinate, triphenyl tin monochloroacetate, triphenyl tin hydroxide and bis(tri-n-butyl tin) oxide as active ingredients.

1 Claim, No Drawings

AQUATIC ORGANISM INHIBITING COMPOSITION

This is a division of application Ser. No. 165,122, filed June 20, 1979, now U.S. Pat. No. 4,318,730.

TECHNOLOGICAL FIELD

The present invention relates to an aquatic organism inhibiting composition comprising N-arylmaleimide as a main active ingredient.

BACKGROUND OF TECHNOLOGY

Shellfish and algae such as *Balanus eburnea; Crassostrea gigas; Mytitus edulis; Tubularia mesembryantemum; Hydroides ezoensis; Dakaria subovoidea; Styela plicate; Bugula neritina; Ulva pertusa; Enteromopha compressa; Ectocarpus indicus,* etc. have been bred on surfaces in water such as a ship bottom, a fishing net, apparatus in sea such as a buoy, a construction in water such as a dam apparatus, a waterway for cooling water used in a condenser of a heat power plant or in a heat-exchanger for various industries, whereby a deceleration of ship speed and excess consumption of a fuel are caused and also economical losses of a cost for cleaning a ship bottom and a loss for a suspension of a ship service during the cleaning term are caused; a handling trouble is caused for constructions in water; and a rate of water supply is decreased to decrease a cooling coefficient and functions of equipments are damaged by organism mass peeled off from walls of a waterway in the waterway for a condenser or a heat exchanger. It has caused serious losses.

Thus, in order to prevent such trouble caused by the breeding and the adhesion of noxious aquatic organisms in sea water or fresh water, it has been proposed to use adhesion inhibiting paints containing a heavy metal compound such as copper oxides, mercury oxides; an organo-tin oxide such as tributyl-tin oxide; an organic chlorine-containing compound and an organic sulfur-containing compounds, or an arsenic compound such as phenarsazine chloride etc.

In the waterway for the cooling water, chlorine or formaline is directly added in the water.

However, the adhesion inhibiting paints containing the heavy metal compound such as copper oxides and mercury oxides have low stability in a storage because the heavy metal oxide is reactive with the varnish component in the composition.

In the polluted sea such as harbor to which industrial discharged water is flowed, hydrogen sulfide is generated by microorganism and the heavy metal compound is discolored and deteriorated to lose the effect.

The copper compounds and the mercury inorganic compound are effective against aquatic organisms such as Balanus, Styela, Coelenterata, Dakaria, etc. however, they are not effective against algae.

When the adhesion inhibiting composition is coated on a substrate made of light metal such as aluminum and magnesium, the heavy metal such as copper and mercury is deposited on the substrate to electrochemically accelerate the corrosion of the substrate. This is another disadvantage.

The adhesion inhibiting paints containing the organo-tin compound such as tributyl tin oxide have inferior effect to those of the adhesion inhibiting paints containing the copper compound or the mercury compound, and also they are expensive. When a large amount of the organo-tin compound is mixed, the characteristics of the coated film is deteriorated and bad smell is caused in the handling.

The adhesion inhibiting paints containing the organic chlorine-containing compound or the organic sulfur-containing compound have inferior effects comparing with the other adhesion inhibiting paints. For example, even though they are effective for Dakaria, they are not effective for Balanus. The effect to noxious aquatic organisms is selective whereby it is difficult to use them in practical applications.

Phenarsazine chloride is toxic to human body, and stimulates mucous membrane whereby the preparation of the adhesion inhibiting paint containing phenarsazine chloride and the coating operation are not easy. When chlorine or formaline is added to water in the waterway for the cooling water, the cooling apparatus is corroded and the effect for inhibiting the adhesion of aquatic organisms is inferior.

The inventors have studied to obtain an improved adhesion inhibiting paint for which has not disadvantages of the convention adhesion inhibiting paints. As the results, the inventors have found that N-arylmaleimides impart effect for inhibiting an adhesion of aquatic organisms for an adhesion inhibiting paint and have proposed them in Japanese Patent Application No. 81476/1976.

These N-arylmaleimides have excellent effect for inhibiting an adhesion of algae, but have slightly inferior effect for inhibiting an adhesion of shellfish. The inventors have further studied to obtain an aquatic organism inhibiting composition for inhibiting an adhesion of both of shellfish and algae.

Resultingly, it has been found, surprisingly, the fact that excellent effects for inhibiting adhesion of both of shellfish and algae could be attained by combining the N-arylmaleimide with a small amount of at least one of organo-tin compound selected from the group consisting or bis(tri-n-butyl tin)mesodibromosuccinate, triphenyl tin monochloroacetate, triphenyl tin hydroxide and bis(tri-n-butyl tin) oxide as active ingredients and if necessary, a small amount of at least one of a compound selected from the group consisting of 4-anilino-monochloroacetylanilide, 2,4-dinitrophenylthiocyanate, 4,6-dinitro-o-cresol and zinc oxide.

DESCRIPTION OF THE INVENTION

The present invention relates to an aquatic organism inhibiting composition comprising at least one of N-arylmaleimide having the formula

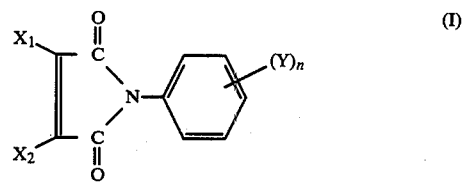

wherein $X_1$ and $X_2$ are the same or different and respectively represent hydrogen or a halogen atom; and Y represents a halogen atom or an alkyl or a lower alkoxy group and n is 0 or an integer of 1 to 3, and a small amount of at least one organo-tin compound selected from the group consisting of bis(tri-n-butyl tin)mesodibromosuccinate, triphenyl tin monochloroacetate, triphenyl tin hydroxide and bis(tri-n-butyl tin)oxide as active ingredients, or an aquatic organism inhibiting composition comprising N-arylmaleimide having the formula

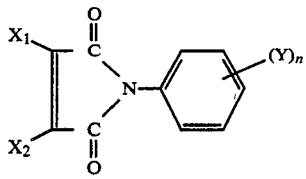

wherein $X_1$ and $X_2$ are the same or different and respectively represent hydrogen or a halogen atom; and Y represents a halogen atom or an alkyl or a lower alkoxy group and n is 0 or an integer of 1 to 3 and a small amount of at least one organo-tin compound selected from the group consisting of bis(tri-n-butyl tin)mesodibromosuccinate, triphenyl tin monochloroacetate, triphenyl tin hydroxide and bis(tri-n-butyl tin)oxide and a small amount of at least one compound selected from the group consisting of 4-anilino-monochloroacetyl anilide, 2,4-dinitrophenylthiocyanate, 4,6-dinitro-o-cresol and zinc oxide (referred to hereinafter as a first group compound) as active ingredients.

Suitable N-arylmaleimides having the formula (I) which are used as the active ingredient of the aquatic organism inhibiting composition of the present invention include N-phenylmaleimide, N-2-(or 3- or 4-)chlorophenylmaleimide, N-3-bromophenylmaleimide, N-4-iodophenylmaleimide, N-4-fluorophenylmaleimide, N-2-(or 3- or 4-)tolylmaleimide, N-4-n-butylphenylmaleimide, N-4-dodecylphenylmaleimide, N-3-methoxyphenylmaleimide, N-4-ethoxyphenylmaleimide, N-3-isopropoxyphenylmaleimide, N-2, 3-(or 2,5-, 3,4- or 3,5-)dichlorophenylmaleimide, N-2,3-(or 2,4-, 2,5-, or 3,5-)xylylmaleimide, N-2,5-dimethoxyphenylmaleimide, N-phenyl-2-bromomaleimide, N-3-chlorophenyl-2-bromomaleimide, N-3-bromophenyl-2-bromomaleimide, N-3,5-dichlorophenyl-2-bromomaleimide, N-phenyl-2,3-dichloromaleimide, N-phenyl-2,3-dibromomaleimide, N-phenyl-2,3-difluoromaleimide, N-2-(or 3- or 4-)chlorophenyl-2,3-dichloromaleimide, N-4-iodophenyl-2,3-dichloromaleimide, N-4-chlorophenyl-2,3-difluoromaleimide, N-4-tolyl-2,3-dibromomaleimide, N-4-methoxyphenyl-2,3-dichloromaleimide, N-3,4-dichlorophenyl-2,3-dichloromaleimide, N-2,5-xylyl-2,3-dichloromaleimide and N-2,4,6-trichlorophenylmaleimide. It is especially preferable to use N-3-chlorophenylmaleimide, N-4-tolylmaleimide, N-isopropoxyphenylmaleimide, N-2,4-xylylmaleimide and N-2,4,6-trichlorophenylmaleimide as a main active ingredient of the aquatic organism inhibiting compositions of the present invention.

The aquatic organism inhibiting composition of the present invention comprises active ingredients ranging 80 to 95 wt.% of at least one of N-arylmaleimides, 20 to 5 wt.% of at least one organo-tin compound or active ingredients ranging 61 to 83 wt.% of at least one N-arylmaleimides, 7 to 9 wt.% of at least one organo-tin compounds and 32 to 8 wt.% of at least one the first group compounds.

The composition is preferably in a form of a paint, a solution or an emulsion comprising less than 60 wt.% especially 10 to 40 wt.% of the active ingredients.

The active ingredients are mixed with suitable film forming composition to prepare an adhesion inhibiting paint. The paint is coated on the ship bottom or the construction in water or the inner wall of an apparatus for passing a cooling water, whereby the adhesion of shellfish or algae on the coated surface can be prevented.

The film forming compositions used in the purposes can be oil varnishes, synthetic resins, and synthetic rubbers. It is possible to blend suitable pigment and filler if desired, in the adhesion inhibiting composition.

The active ingredients for the aquatic organism inhibiting composition are incorporated at less than 60 wt.% preferably 10 to 40 wt.% to the film forming composition.

In order to inhibit the adhesion and growth of aquatic organisms in the passage for the cooling water, it is possible to add the active ingredients in form of emulsion, however, in order to maintain the effect for inhibiting the adhesion for a long time, it is necessary to coat in a form of a paint.

Thus, the aquatic organism inhibiting composition of the present invention can be applied for a fish net regardless of its materials.

BEST MODES OF THE INVENTION

The present invention will be illustrated in detail by Examples and References.

EXAMPLE 1

In a pocket mill, 18.0 wt. parts of N-4-tolylmaleimide, 2.0 wt. parts of bis(tri-n-butyl-tin)mesodibromosuccinate, 10.0 wt.% of red iron oxide, 15.0 wt. parts of talc, 20.0 wt. parts of barium sulfate, 5.5 wt. parts of a vinyl resin, 5.5 wt. parts of rosin, 2.0 wt. parts of tricresyl phosphate, 11.0 wt. parts of methylisobutyl ketone and 11.0 wt. parts of xylene were pulverized, blended and kneaded to prepare an adhesion inhibiting paint.

Each steel plate (300×100×1 mm) was precoated with a wash primer for one time and further coated with a ship bottom coating for two times. Each plate was further coated with the adhesion inhibiting paint by a brush for two times to prepare the sample.

The sample was fitted in a wooden frame and was dipped into sea from a raft for dipping at a depth of 1.5 m.

The samples dipped in a sea were pulled up for specific terms. The ratio of organisms adhered area to the total area of the sample was shown by percentage.

The results after 12 months from the initiation of the immersing are shown in Table 1.

EXAMPLES 2 to 17

In accordance with the process of Example 1 except using various N-arylmaleimides instead of N-4-tolylmaleimide, adhesion inhibiting paints were prepared and the immersing tests were carried out. The results are shown in Table 1.

EXAMPLE 18

In accordance with the process of Example 1 except using 9.0 wt. parts of N-4-tolylmaleimide and 9.0 wt. parts of N-2,4-xylylmaleimide instead of 18.0 wt. parts of N-4-tolylmaleimide and using 2.0 wt. parts of triphenyl tin monochloroacetate instead of 2.0 wt. parts of bis(tri-n-butyl tin)mesodibromosuccinate, an adhesion inhibiting paint was prepared and the immersing tests were carried out.

The results is shown in Table 1.

EXAMPLE 19

In accordance with the process of Example 1 except using 9.0 wt. parts of N-4-tolylmaleimide and 9.0 wt. parts of N-2,4-xylylmaleimide instead of 18.0 wt. parts of N-4-tolylmaleimide and using 1.0 wt. part of bis(tri-n-butyl tin)mesodibromosuccinate and 1.0 wt. part of triphenyl-tin monochloroacetate instead of 2.0 wt. parts of bis(tri-n-butyl tin)mesodibromosuccinate, an adhesion inhibiting paint was prepared and the immersing test was carried out. The result is shown in Table 1.

In accordance with the process of Example 1, an adhesion inhibiting paint was prepared without incorporating the active ingredients and the immersing test was carried out. The result is shown as the reference.

EXAMPLE 20

In a pocket mill, 14.4 wt. parts of N-4-tolylmaleimide, 1.6 wt. parts of bis(tri-n-butyl tin)mesodibromosuccinate, 4.0 wt. parts of 4-anilino-monochloroacetylanilide, 10.0 wt. parts of red iron oxide, 15.0 wt. parts of talc, 20.0 wt. parts of barium sulfate, 5.5 wt. parts of vinyl resin, 5.5 wt. parts of rosin, 2.0 wt. parts of tricresyl phosphate, 11.0 wt. parts of methyl isobutyl ketone and 11.0 wt. parts of xylene were pulverized, blended and kneaded to prepare an adhesion inhibiting paint.

Each steel plate (300×100×1 mm) was precoated with a wash primer for one time and further coated with a ship bottom coating for two times. Each plate was further coated with the adhesion inhibiting paint by a brush for two times to prepare the sample.

The sample was fitted in a wooden frame and was dipped into sea from a raft for dipping at a depth of 1.5 m.

The samples dipped in sea were pulled up for specific terms. The ratio of organisms adhered area to the total area of the sample was shown by percentage.

The results after 12 months from the initiation of the immersing are shown in Table 2.

In accordance with the process of Example 1, the immersing tests were carried out.

The result is shown in Table 2.

EXAMPLES 21 to 36

In accordance with the process of Example 20 except using various N-arylmaleimides instead of N-4-tolylmaleimide, adhesion inhibiting paints were prepared and the immersing tests were carried out. The results were shown in Table 2.

EXAMPLE 37

In accordance with the process of Example 20 except using 7.2 wt. parts of N-4-tolylmaleimide and 7.2 wt. parts of N-2,4-xylylmaleimide instead of 14.4 wt. parts of N-4-tolylmaleimide, and using 4.0 wt. parts of 2,4-dinitrophenylthiocyanate instead of 4.0 wt. parts of 4-anilino-monochloroacetylanilide, an adhesion inhibiting paint was prepared and the immersing tests was carried out.

The result is shown in Table 2.

EXAMPLE 38

In accordance with the process of Example 20 except using 7.2 wt. parts of N-4-tolylmaleimide and 7.2 wt. parts of N-2,4-xylylmaleimide instead of 14.4 wt. parts of N-4-tolylmaleimide and using 0.8 wt. part of bis(tri-n-butyl tin)mesodibromosuccinate and 0.8 wt. part of triphenyl-tin monochloroacetate instead of 1.6 wt. parts of bis(tri-n-butyl tin)mesodibromosuccinate and using 4.0 wt. parts of 2,4-dinitrophenylthiocyanate instead of 4.0 wt. parts of 4-anilinomonochloroacetylanilide, an adhesion inhibiting paint was prepared and the immersing test was carried out. The result is shown in Table 2.

In accordance with the process of Example 20, an adhesion inhibiting paint was prepared without incorporating the active ingredients and the immersing test was carried out. The result is shown as the reference.

REFERENCE 1

In a pocket mill, 20.0 wt. parts of N-4-tolylmaleimide, 10.0 wt. parts of red iron oxide, 15.0 wt. parts of talc, 20.0 wt. parts of barium sulfate, 5.5 wt. parts of vinyl resin, 5.5 wt parts of rosin, 2.0 wt. parts of tricresyl phosphate, 11.0 wt. parts of methylisobutyl ketone and 11.0 wt. parts of xylene were pulverized, blended and kneaded to prepare an adhesion inhibiting paint.

Each steel plate (300×100×1 mm) was precoated with a wash primer for one time and further coated with a ship bottom coating for two times. Each plate was further coated with the adhesion inhibiting paint by a brush for two times to prepare the sample.

The sample was fitted in a wooden frame and was dipped into sea from a raft for dipping at a depth of 1.5 m.

The samples dipped in sea were pulled up for specific terms. The ratio of organisms adhered area to the total area of the sample was shown by percentage.

The results after 12 months from the initiation of the immersing are shown in Table 3.

REFERENCES 2 to 25

In accordance with the process of Reference 1 except using various N-arylmaleimides (I) instead of N-4-tolylmaleimide and using bis(tri-n-butyl tin)mesodibromosuccinate, triphenyl tin monochloroacetate, triphenyl tin hydroxide, bis(tri-n-butyl tin)oxide, 4-anilinomonochloroacetylanilide, 2,4-dinitrophenylthiocyanate, 4,6-dinitro-o-cresol or zinc oxide, adhesion inhibiting paints were prepared and the immersing tests were carried out. The results were shown in Table 3.

In accordance with the process of Reference 1, an adhesion inhibiting paint was prepared without incorporating the active ingredients and the immersing test was carried out. The results are shown as the control.

TABLE 1

| Example | Active ingredient N—arylmaleimide (I) | Organo-tin compound | Adhered are (%) Algae | Shellfish |
|---|---|---|---|---|
| 1 | Compound I-1 | Compound II-1 | 5 | 5 |
| 2 | Compound I-2 | " | 10 | 29 |
| 3 | Compound I-3 | " | 5 | 10 |
| 4 | Compound I-4 | " | 4 | 14 |
| 5 | Compound I-5 | " | 5 | 13 |
| 6 | Compound I-6 | " | 4 | 12 |
| 7 | Compound I-7 | " | 6 | 12 |
| 8 | Compound I-8 | " | 13 | 21 |

TABLE 1-continued

| | Active ingredient | | Adhered are (%) | |
|---|---|---|---|---|
| Example | N—arylmaleimide (I) | Organo-tin compound | Algae | Shellfish |
| 9 | Compound I-9 | " | 10 | 18 |
| 10 | Compound I-10 | " | 11 | 21 |
| 11 | Compound I-11 | " | 7 | 25 |
| 12 | Compound I-12 | " | 7 | 14 |
| 13 | Compound I-13 | " | 7 | 22 |
| 14 | Compound I-14 | " | 8 | 20 |
| 15 | Compound I-15 | " | 5 | 15 |
| 16 | Compound I-16 | " | 4 | 20 |
| 17 | Compound I-17 | " | 1 | 3 |
| 18 | Compound I-1 / Compound I-5 | Compound II-2 | 6 | 19 |
| 19 | Compound I-1 / Compound I-5 | Compound II-1 / Compound II-2 | 6 | 12 |
| Control | none | none | *— | 100 | note:
*In a middle term, more than 80% of the area was covered with algae. After 6 months, shellfish were adhered and algae was removed from the surface of the test piece and was adhered on the shellfish.

TABLE 2

| | Active ingredient | | | Adhered are (%) | |
|---|---|---|---|---|---|
| Example | N—aryl-maleimide | Organo-tin comp. | Group 1 compound | Algae | Shellfish |
| 20 | Comp. I-1 | Comp. II-1 | Comp. III-1 | 2 | 5 |
| 21 | Comp. I-2 | " | " | 10 | 28 |
| 22 | Comp. I-3 | " | " | 3 | 5 |
| 23 | Comp. I-4 | " | " | 3 | 9 |
| 24 | Comp. I-5 | " | " | 4 | 7 |
| 25 | Comp. I-6 | " | " | 4 | 10 |
| 26 | Comp. I-7 | " | " | 5 | 10 |
| 27 | Comp. I-8 | " | " | 10 | 15 |
| 28 | Comp. I-9 | " | " | 9 | 14 |
| 29 | Comp. I-10 | " | " | 7 | 16 |
| 30 | Comp. I-11 | " | " | 7 | 24 |
| 31 | Comp. I-12 | " | " | 5 | 12 |
| 32 | Comp. I-13 | " | " | 5 | 17 |
| 33 | Comp. I-14 | " | " | 6 | 14 |
| 34 | Comp. I-15 | " | " | 5 | 18 |
| 35 | Comp. I-16 | " | " | 4 | 13 |
| 36 | Comp. I-17 | " | " | 0 | 0 |
| 37 | Comp. I-1 / Comp. I-5 | " | Comp. III-2 | 0 | 2 |
| 38 | Comp. I-1 / Comp. I-5 | Comp. II-1 / Comp. II-2 | Comp. III-2 / Comp. III-3 | 7 | 10 |
| Control | none | none | none | *— | 100 | note:
*In a middle term, more than 80% of the area was covered with algae. After 6 months, shellfish were adhered and algae was removed from the surface of the test piece and was adhered on the shellfish.

TABLE 3

| | | Adhered area (%) | |
|---|---|---|---|
| Reference | Active ingredient | Algae | Shellfish |
| 1 | Compound I-1 | 10 | 30 |
| 2 | Compound I-2 | 15 | 40 |
| 3 | Compound I-3 | 10 | 20 |
| 4 | Compound I-4 | 10 | 25 |
| 5 | Compound I-5 | 15 | 30 |
| 6 | Compound I-6 | 10 | 20 |
| 7 | Compound I-7 | 10 | 25 |
| 8 | Compound I-8 | 20 | 40 |
| 9 | Compound I-9 | 15 | 30 |
| 10 | Compound I-10 | 13 | 30 |
| 11 | Compound I-11 | 10 | 35 |
| 12 | Compound I-12 | 20 | 30 |
| 13 | Compound I-13 | 15 | 30 |
| 14 | Compound I-14 | 14 | 31 |
| 15 | Compound I-15 | 14 | 30 |
| 16 | Compound I-16 | 6 | 30 |
| 17 | Compound I-17 | 4 | 15 |
| 18 | Compound I-18 | 5 | 15 |
| 19 | Compound II-1 | 15 | 5 |
| 20 | Compound II-2 | 20 | 5 |
| 21 | Compound II-3 | 20 | 7 |
| 22 | Compound II-4 | 35 | 5 |
| 23 | Compound III-1 | 40 | 45 |
| 24 | Compound III-2 | 25 | 35 |
| 25 | Compound III-3 | 60 | 40 |
| Control | | *— | 100 | note:
*In a middle term, more than 80% of the area was covered with algae. After 6 months, shellfish were adhered and algae was removed from the surface of the test piece and was adhered on the shellfish.

N-arylmaleimides (I)

Compound I-1: N-4-tolylmaleimide
Compound I-2: N-phenylmaleimide
Compound I-3: N-3-i-propoxyphenylmaleimide Compound I-4: N-2,5-dichlorophenylmaleimide
Compound I-5: N-2,4-xylylmaleimide
Compound I-6: N-2,5-xylylmaleimide
Compound I-7: N-2,5-dimethoxyphenylmaleimide
Compound I-8: N-phenyl-2-bromomaleimide
Compound I-9: N-3-chlorophenyl-2-bromomaleimide
Compound I-10: N-3,5-dichlorophenyl-2-bromomaleimide
Compound I-11: N-phenyl-2,3-dichloromaleimide
Compound I-12: N-4-chlorophenyl-2,3-dichloromaleimide
Compound I-13: N-4-tolyl-2,3-dibromomaleimide
Compound I-14: N-4-methoxyphenyl-2,3-dibromomaleimide
Compound I-15: N-3,4-dichlorophenyl-2,3-dichloromaleimide
Compound I-16: N-2,5-xylyl-2,3-dichloromaleimide
Compound I-17: N-2,4,6-trichlorophenylmaleimide
Compound I-18: N-3-chlorophenylmaleimide Organo-tin Compounds Compound II-1: bis(tri-n-butyl tin)mesodibromosuccinate
Compound II-2: triphenyl-tin monochloroacetate
Compound II-3: triphenyl-tin hydroxide
Compound II-4: bis(tri-n-butyl tin)oxide Group 1 Compounds Compound III-1: 4-anilino-monochloroacetylanilide
Compound III-2: 2,4-dinitrophenylthiocyanate
Compound III-3: zinc oxide
Compound III-4: 4,6-dinitro-o-cresol

EXAMPLES 39 to 42

In accordance with the process of Example 1 except using various N-arylmaleimides instead of N-4-tolylmaleimide and using various organo-tin compounds instead of bis(tri-n-butyl tin)mesodibromosuccinate, adhesion inhibiting paints were prepared and the immersing tests were carried out. The results are shown in Table 4.

EXAMPLES 43 to 48

In accordance with the process of Example 20 except using various N-arylmaleimides instead of N-4-tolylmaleimide and using various organo-tin compounds instead of bis(tri-n-butyl-tin)mesodibromosuccinate and using 4-anilinomonochloroacetylanilide, 2,4-dinitrothiocyanate, 4,6-dinitro-o-cresol or zinc oxide, adhesion inhibiting paints were prepared and the immersing tests were carried out. The results are shown in Table 4.

In accordance with the process of Example 20, an adhesion inhibiting paint was prepared without incorporating the active ingredients and the immersing test was carried out. The results are shown as the control.

TABLE 4

| Example | 39 | 40 | 41 | 42 | 43 | 44 |
|---|---|---|---|---|---|---|
| N—arylmaleimide | Comp. I-18 | Comp. I-18 | Comp. I-18 | Comp. I-1 | Comp. I-18 | Comp. I-18 |
| Organo-tin Comp. | Comp. II-3 | Comp. II-4 | Comp. II-1 | Comp. II-2 | Comp. II-3 | Comp. II-4 |
| Group 1 Comp. | none | none | none | none | Comp. III-1 | Comp. III-1 |
| 6 month | | | | | | |
| Algae | 0 | 0 | 0 | 0 | 0 | 0 |
| Shellfish | 0 | 0 | 0 | 0 | 0 | 0 |
| 8 month | | | | | | |
| Algae | 0 | 0 | 0 | 0 | 0 | 0 |
| Shellfish | 2 | 0 | 0 | 2 | 0 | 0 |
| 10 month | | | | | | |
| Algae | 2 | 2 | 0 | 4 | 2 | 2 |
| Shellfish | 5 | 5 | 0 | 7 | 1 | 1 |
| 12 month | | | | | | |
| Algae | 4 | 5 | 2 | 10 | 5 | 6 |
| Shellfish | 12 | 8 | 0 | 16 | 3 | 3 |

| Example | 45 | 46 | 47 | 48 | Control |
|---|---|---|---|---|---|
| N—arylmaleimide | Comp. I-1 | Comp. I-18 | Comp. I-5 | Comp. I-1 | none |
| Organo-tin Comp. | Comp. II-2 | Comp. II-1 | Comp. II-1 | Comp. II-2 | none |
| Group 1 Comp. | Comp. III-2 | Comp. III-1 | Comp. III-4 | Comp. III-3 | none |
| 6 month | | | | | |
| Algae | 0 | 0 | 0 | 0 | 80 |
| Shellfish | 0 | 0 | 0 | 0 | 5 |
| 8 month | | | | | |
| Algae | 0 | 0 | 0 | 0 | 20 |
| Shellfish | 0 | 0 | 0 | 0 | 37 |
| 10 month | | | | | |
| Algae | 0 | 0 | 9 | 0 | 5 |
| Shellfish | 0 | 0 | 1 | 0 | 82 |
| 12 month | | | | | |
| Algae | ) | ) | 10 | 0 | *— |
| Shellfish | 0 | 0 | 1 | 0 | 100 |

INDUSTRIAL UTILITIES

In industries, the aquatic organism inhibiting compositions of the present invention can be used for preventing adhesion and growth of aquatic organisms by preparing an adhesion inhibiting paint by incorporating the composition in a film forming composition and coating the paint on a ship bottom, a construction in water or a wall in a waterway for cooling water.

We claim:

1. An aquatic organism inhibiting composition in the form of a paint, solution or emulsion which comprises 80-95 wt. percent of at least one N-arylmaleimide having the formula

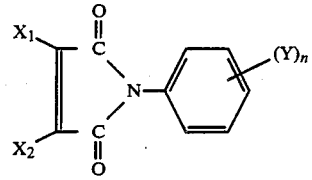

wherein $X_1$ and $X_2$ are the same or different and respectively represent hydrogen or a halogen atom; and Y represents a halogen atom or a lower alkyl or a lower alkoxy group and n is 0 or an integer of 1 to 3 and 5-20 wt. percent of at least one organo-tin compound selected from the group consisting of bis(tri-n-butyl tin)-mesodibromosuccinate, triphenyl tin monochloroacetate, triphenyl tin hydroxide and bis(tri-n-butyl tin)oxide.

* * * * *